(12) United States Patent
Saud et al.

(10) Patent No.: US 6,706,899 B2
(45) Date of Patent: Mar. 16, 2004

(54) ACYCLIC CHIRAL COMPOUND FROM GARCINIA ACID AND PROCESS FOR PREPARING THE SAME

(75) Inventors: Ibrahim Ibnu Saud, Kerala (IN); Tom Thomas Puthiyaparampil, Kerala (IN)

(73) Assignee: Department of Science and Technology, Technology Bhavan, New Delhi (IN)

( * ) Notice: Subject to any disclaimer, the term of this patent is extended or adjusted under 35 U.S.C. 154(b) by 142 days.

(21) Appl. No.: 09/946,816

(22) Filed: Sep. 5, 2001

(65) Prior Publication Data

US 2002/0042528 A1 Apr. 11, 2002

(30) Foreign Application Priority Data

Oct. 3, 2000  (IN) ...................................... 883/DEL/2000

(51) Int. Cl.$^7$ ..................... C07D 317/14; C07C 69/66
(52) U.S. Cl. ..................... 549/450; 549/453; 560/182
(58) Field of Search ................. 549/450, 453; 560/182

(56) References Cited

U.S. PATENT DOCUMENTS

| | | | |
|---|---|---|---|
| 3,764,692 A | * | 10/1973 | Lowenstein |
| 6,127,553 A | | 10/2000 | Ibnusaud et al. |
| 6,147,228 A | | 11/2000 | Ibnusaud et al. |
| 6,489,492 B2 | | 12/2002 | Saud et al. |
| 6,489,493 B2 | | 12/2002 | Saud et al. |

OTHER PUBLICATIONS

Ibnusaud, I. et al. "Chiral γ–butyrolactones related to optically active 2–hydroxycitric acids." Tetrahedron vol. 58 (2002) pp. 4887–4892.

Jena, B.S. et al. "Chemistry and Biochemistry of (–)–Hydroxycitric Acid from Garcinia." Journal of Agricultural and Food Chemistry vol. 50 (2002) pp. 10–22.

Narasaka, K. et al. "Use of 1,3–Oxazolidin–2–one Derivatives of 3–Borylpropenoic Acids as β–Hydroxy Acrylic Acid Equivalents in the Asymmetric Diels–Alder Reaction Catalyzed by a Chiral Titanium Reagent." Tetrahedron vol. 48, No. 27 (1992) pp. 5743–5754.

Seebach, D. et al. "TADDOLs, Their Derivatives and TADDOL Analogues: Versatile Chiral Auxiliaries." Agnew Chem. Int. Ed. vol. 40 (2001) pp. 92–138.

* cited by examiner

Primary Examiner—Taofiq Solola
(74) Attorney, Agent, or Firm—Sidley Austin Brown & Wood LLP

(57) ABSTRACT

The present invention relates to a novel acyclic chiral compound of Garcinia acid of formula I,

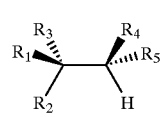

Formula I Wherein:

$R_2=R_5$=lower aryl ester or alkyl ester or substituted aryl alcohol or alkyl alcohol $R_3$=substituted aryl ester or alkyl ester or substituted aryl alcohol $R_1=R_4$=hydroxyl or

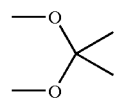

And a process for preparing the same

23 Claims, No Drawings

ACYCLIC CHIRAL COMPOUND FROM GARCINIA ACID AND PROCESS FOR PREPARING THE SAME

BACKGROUND OF THE INVENTION

Garcinia acid [(−)-Hydroxycitric acid lactone or (2S,3S)-Tetrahydro-3-hydroxy-5-oxo-2,3-furandicarboxylic acid] is isolated from the fruits of *Garcinia cambogia, Garcinia indica* and *Garcinia atroviridis*. This molecule is widely used as an important ingredient in many pharmaceutical formulations.

The non-availability of Garcinia acid in the market, in the pure form, has resulted in the limited use of these compounds in the area of organic synthesis and pharmaceutical front. This is due to the lack of any commercially viable large-scale manufacturing process. In U.S. patent application Ser. No. 09/365,300 economic, commercially viable, cost effective process for the large-scale isolation of Garcinia acid has been described.

The object of the present invention is to prepare hitherto unknown acyclic chiral molecules from Garcinia acid.

To achieve the said objective this invention provides novel chiral derivatives of Garcinia acid of formula I

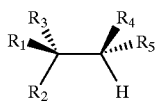

Formula I wherein:
$R_2 = R_5$ = lower aryl/alkyl ester or substituted aryl/alkyl alcohol
$R_3$ = substituted aryl/alkyl ester or substituted aryl alcohol
$R_1 = R_4$ = hydroxyl or

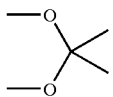

In the above formula I $R_2$ and $R_5$ is selected from —COOCH$_3$, —COOC$_2$H$_5$, —COOCH(CH$_3$)$_2$, —C(Ph)$_2$OH, —C(4-MePh)$_2$OH, —C(1-Naphth)$_2$OH $R_1$ and $R_4$ is OH or

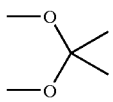

$R_3$ is selected from —CH$_2$COOCH$_3$, —CH$_2$COOC$_2$H$_5$, —CH$_2$COOCH(CH$_3$)$_2$, —CH$_2$C(Ph)$_2$OH, —CH$_2$C(4-MePh)$_2$OH, —CH$_2$C(1-Naphth)$_2$OH to form various chiral derivatives, namely, chiral triesters, chiral ketals and chiral alcohols.

Chiral triester derivatives:

$R_2 = R_5 =$ —COOCH$_3$, $R_1 = R_4 =$ —OH and $R_3 =$ —CH$_2$COOCH$_3$ $R_2 = R_5 =$ —COOC$_2$H$_5$; $R_1 = R_4 =$ —OH; $R_3 =$ —CH$_2$COOC$_2$H$_5$ $R_2 = R_5 =$ —COOCH(CH$_3$)$_2$; $R_1 = R_4 =$ —OH; $R_3 =$ —CH$_2$COOCH(CH$_3$)$_2$ Chiral ketal derivatives:

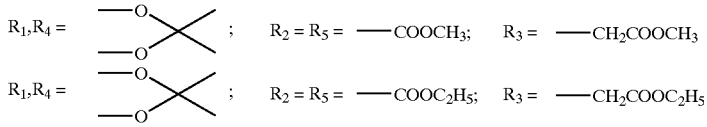

Chiral alcohol derivatives (diols):

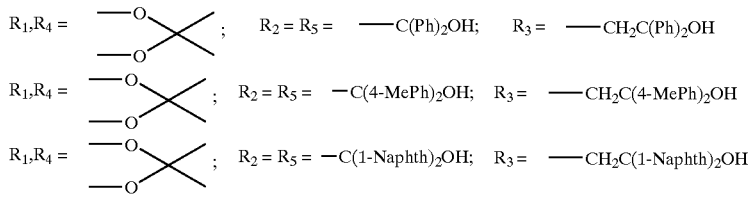

Summary of the chiral derivatives of Garcinia acid is given below in scheme I:

SCHEME I

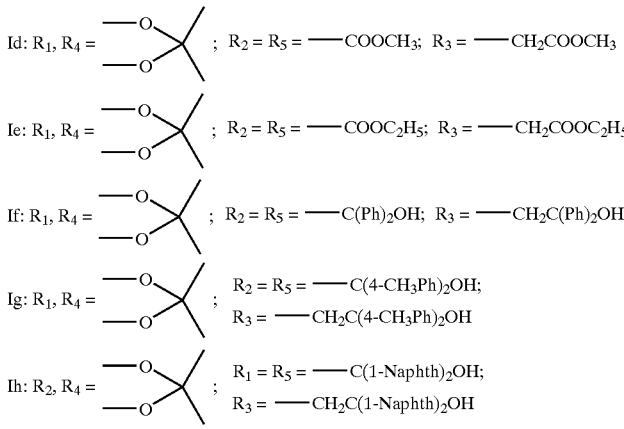

Ia: $R_2 = R_5 =$ —COOCH$_3$; $R_1 = R_4 =$ —OH; $R_3 =$ —CH$_2$COOCH$_3$

Ib: $R_2 = R_5 =$ —COOC$_2$H$_5$; $R_1 = R_4 =$ —OH; $R_3 =$ —CH$_2$COOC$_2$H$_5$

Ic: $R_2 = R_5 =$ —COOCH(CH$_3$)$_2$; $R_1 = R_4 =$ —OH; $R_3 =$ —CH$_2$COOCH(CH$_3$)$_2$

Id: $R_1, R_4 =$ [acetonide]; $R_2 = R_5 =$ —COOCH$_3$; $R_3 =$ —CH$_2$COOCH$_3$ Ie: $R_1, R_4 =$ [acetonide]; $R_2 = R_5 =$ —COOC$_2$H$_5$; $R_3 =$ —CH$_2$COOC$_2$H$_5$ If: $R_1, R_4 =$ [acetonide]; $R_2 = R_5 =$ —C(Ph)$_2$OH; $R_3 =$ —CH$_2$C(Ph)$_2$OH Ig: $R_1, R_4 =$ [acetonide]; $R_2 = R_5 =$ —C(4-CH$_3$Ph)$_2$OH; $R_3 =$ —CH$_2$C(4-CH$_3$Ph)$_2$OH Ih: $R_2, R_4 =$ [acetonide]; $R_1 = R_5 =$ —C(1-Naphth)$_2$OH; $R_3 =$ —CH$_2$C(1-Naphth)$_2$OH The present invention further provides a process for preparing the chiral triester derivatives of formulae comprising:
  refluxing garcinia acid with appropriate alcohol in presence of an inorganic catalyst for 6–12 hours,
  adjusting the pH of the reaction-mixture using aqueous alkali solution,
  concentrating the said reaction-mixture by evaporation,
  extracting the said concentrate with an organic solvent,
  The said appropriate alcohols are selected from methanol, ethanol and isopropanol.
  The said catalyst is conc.HCl.
  The said organic solvent is chloroform.
  The present invention further includes a process for preparing the chiral alcohol derivatives of formulae If to Ih comprising:
  adding solution of chiral acetal/ketal in an organic solvent to a solution of appropriate grignard reagent(ArMgX) in an organic solvent,
  refluxing the mixture for 10–20 hours,
  adding the inorganic salt solution to the chilled reaction mixture,
  collecting the organic phase and extracting the aqueous layer further with an organic acid,
  drying the organic extract using an inorganic salt,
  evaporating the said extract,
  subjecting the residue to chromatography.
  The organic solvent is tetra hydro furan (THF).
  The said appropriate grignard reagent is phenyl Mg bromide, methylphenyl Mg bromide, naphthyl Mg bromide.
  The said inorganic salt is ammonium chloride and organic solvent used for extraction is ether.
  The salt used for drying the extract is sodium sulphate.
  The chromatography employed for purification is column chromatography.

The gel used for chromatography is silica gel.
The eluant used for chromatography is hexane-chloroform mixture.
Chiral ketals were prepared using standard procedures.
The invention will now be described with reference to the following examples:
Chiral triester derivatives:

EXAMPLE 1

Trimethyl (1S,2S)-1,2-dihydroxy-1,2,3-propanetricarboxylate (Ia)

Garcinia acid (5.0 g, 26.3 mmol) was refluxed with methanol (100 ml) and conc. HCl (3 ml) for 12 hours. pH of the reaction mixture was adjusted to neutral using aqueous solution of sodium bicarbonate. The resultant solution was evaporated and extracted with chloroform (4×50 ml). The combined chloroform extracts was dried (sodium sulphate) and on concentration furnished Ia.
Yield: 2.0 g (30%)

EXAMPLE 2

Triethyl (1S,2S)-1,2-dihydroxy-1,2,3-propanetricarboxylate (Ib)

Ib was prepared from Garcinia acid and ethanol in 46% yield by the same procedure used to prepare Ia from Garcinia acid.

EXAMPLE 3

Triisopropyl (1S,2S)-1,2-dihydroxy-1,2,3-propanetricarboxylate (Ic)

Ic was prepared from Garcinia acid and dry isopropanol by the same procedure used to prepare Ia from Garcinia acid.

EXAMPLE 4

Dimethyl(4S,5S)-2,2-dimethyl-4-(2-oxo-2-methoxyethyl)-1,3-dioxolane-4,5-dicarboxylate (Id)

To Ia (2.0 g, 8 mmol) in dry acetone (50 ml), anhydrous copper sulphate (1.0 g) and a few drops of conc. sulphuric acid were added. The mixture was refluxed for four hours, followed by filtration and neutralisation using aqueous sodium bicarbonate solution. The resultant solution obtained after evaporation was extracted with hexane (4×25 ml). The combined extracts after washing with water (50 ml) was dried with sodium sulphate. Upon evaporation, Id obtained as an yellow oil.

Yield: 0.5 g (22%)

EXAMPLE 5

Diethyl (4S,5S)-2,2-dimethyl-4-(2-oxo-2-ethoxyethyl)-1,3-dioxolane-4,5-dicarboxylate (Ie)

Ie was prepared from Ib in 44% yield by the same procedure used to prepare Id from Ia.

EXAMPLE 6

(4S,5S)-4-(2-hydroxy-2,2-diphenylethyl)-2,2-dimethyl-alpha, alpha,alpha',alpha'-tetraphenyl-1,3-dioxolane-4,5-dimethanol (If)

A solution of Id (1 g, 3.4 mmol, in 7 ml THF) was added to a solution of Phenyl magnesium bromide in THF (20 ml, 1M) and the mixture was refluxed for 15 hours. To the chilled reaction mixture aqueous ammonium chloride solution (20 ml) was added. The organic phase was collected and the aqueous layer was extracted with ether (5×10 ml). The combined organic phase was dried (sodium sulphate). The solution upon evaporation followed by column chromatography (silica gel 60–120 mesh, eluent: hexane) yielded If.

Yield: 1.0%

USES pharmaceutical applications chiral derivatives Ia-Ic and If-Ih is used for the preparation of chiral catalyst and chiral auxiliaries.

The derivatives of Ia-Ih is used as chiral synthons

We claim:

1. A novel acyclic chiral compound of Garcinia acid of formula I,

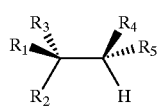

Formula I wherein:

$R_2=R_5$=lower aryl ester or alkyl ester or substituted aryl alcohol or alkyl alcohol $R_3$=substituted aryl ester or substituted alkyl ester or substituted aryl alcohol $R_1=R_4$=hydroxyl or =$R_1$ and $R_4$ together form

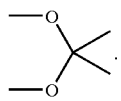

2. A compound as claimed in claim 1 wherein, $R_2$ and $R_5$ is selected from —COOCH$_3$, —COOC$_2$H$_5$, —COOCH(CH$_3$)$_2$, —C(Ph)$_2$OH, —C(4—MePh)$_2$OH, —C(1-Naphthh)$_2$OH $R_1$ and $R_4$ is OH or $R_1$ and $R_4$ together form

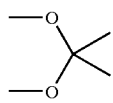

$R_3$ is selected from —CH$_2$COOCH$_3$, —CH$_2$COOC$_2$H$_5$, —CH$_2$COOCH(CH$_3$)$_2$, —CH$_2$C(Ph)$_2$OH, —CH$_2$C(4-MePh)$_2$OH, —CH$_2$C(1-Naphth)2OH.

3. A compound as claimed in claim 2 wherein, $R_2$=$R_5$=—COOCH$_3$, $R_1$=$R_4$=—OH and $R_3$=—CH$_2$COOCH$_3$ and said compound is Trimethyl (1S,2S)-1,2-dihydroxy-1, 2,3-propanetricarboxylate

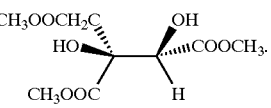

4. A compound as claimed in claim 2 wherein, $R_2$=$R_5$=—COOC$_2$H$_5$; $R_1$=$R_4$=—OH; $R_3$=—CH$_2$COOC$_2$H$_5$ and said compound is Triethyl (1S,2S)-1,2-dihydroxy-1,2,3-propanetricarboxylate

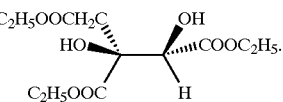

5. A compound as claimed in claim 2 wherein, $R_2$=$R_5$=—COOCH(CH$_3$)$_2$, $R_1$=$R_4$=—OH; $R_3$=-CH$_2$COOCH(CH$_3$)$_2$ and said compound is Triisopropyl(1S,2S)-1,2-dihydroxy-1,2,3-propanetricarboxylate

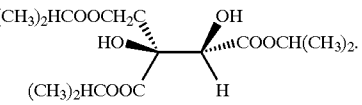

6. A compound as claimed in claim 2 wherein, =$R^1$ and $R_4$ together form

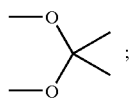

$R_2$=$R_5$=—COOCH$_3$; $R_3$=—CH$_2$COOC$_2$H$_5$ and said compound is Dimethyl(4S,5S)-2,2-dimethyl-4-(2-oxo-2-methoxyethyl) -1,3-dioxolane-4,5-dicarboxylate

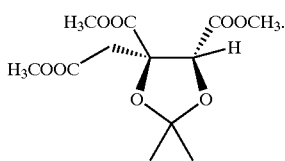

7. A compound as claimed in claim 2 wherein, $R_4=R_1$ and $R_4$ together form

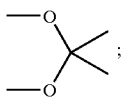

$R_2=R_5=$—$COOC_2H_5$; $R_3=$—$CH_2COOC_2H_5$ and said compound is Diethyl (4S,5S)-2,2-dimethyl-4-(2-oxo-2-ethoxyethyl)-1,3-dioxolane-4,5-dicarboxylate

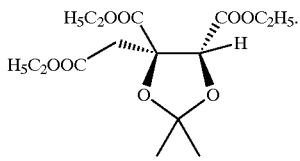

8. A compound as claimed in claim 2 wherein $R_4=R_1$ and $R_4$ together form

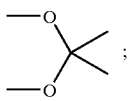

$R_2=R_5=$—$C(Ph)_2OH$; $R_3$—$CH_2C(Ph)_2OH$ and said compound is (4S,5S)-4-(2-hydroxy-2,2-diphenylethyl)-2,2-diphenylethyl)-2,2-dimethyl-alpha,alpha,alpha',alpha'-tetraphenyl-1,3-dioxolane-4,5-dimethanol

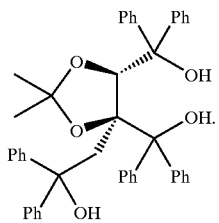

9. A compound as claimed in claim 2 wherein, $R_4=R_1$ and $R_4$ together form

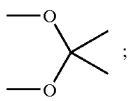

$R_2=R_5=$—$C(4-MePh)_2OH$; $R_3=$—$CH_2C(4-MePh)_2OH$

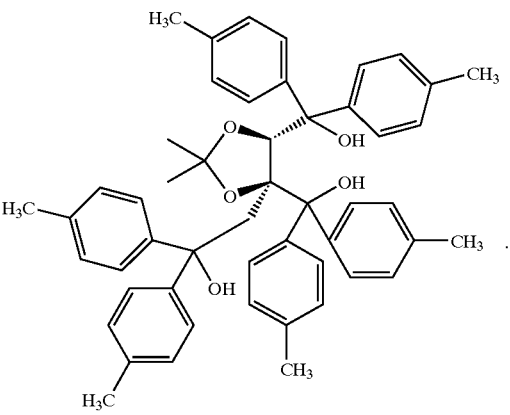

10. A compound as claimed in claim 2 wherein, $R_4=R_1$ and $R_4$ together form

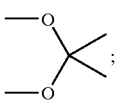

$R_1=R_5=$—$C(1-Naphth)_2OH$; $R_3=$—$CH_2C(1-Naphth)_2OH$

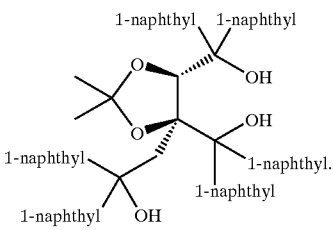

11. A process for preparing the chiral triesters derivatives of formula I claimed in claim 1 comprising:

refluxing garcinia acid with appropriate alcohol in presence of an inorganic catalyst for 6–12 hours, adjusting the pH of the reaction-mixture using aqueous alkali solution, concentrating the said reaction-mixture by evaporation, extracting the said concentrate with an organic solvent.

12. A process as claimed in claim 11 wherein, the said appropriate alcohols is selected from methanol, ethanol and isopropanol.

13. A process as claimed in claim 11 wherein, the said catalyst is concentrated 1-ICI.

14. A process as claimed in claim 11 wherein, the said organic solvent is chloroform.

15. A process for preparing the chiral alcohols of formula I as claimed in claim 1 comprising:

adding solution of chiral acetal or ketal in an organic solvent to a solution of appropriate grignard reagent (ArMgX) in an organic solvent, refluxing the mixture for 10–20 hours, adding the inorganic salt solution to the chilled reaction mixture, collecting the organic phase and extracting the aqueous layer further with an organic acid, drying the organic extract using an inorganic salt, evaporating the said extract, subjecting the residue to chromatography.

16. A process as claimed in claim 15 wherein, the organic solvent is tetrahydrofuran (THF).

17. A process as claimed in claim 15 wherein, the said appropriate grignard reagent is phenyl Mg bromide, methylphenyl Mg bromide, naphthyl Mg bromide.

18. A process as claimed in claim 15 wherein, the said inorganic salt is ammonium chloride.

19. A process as claimed in claim 15 wherein, the said organic solvent used for extraction is ether.

20. A process as claimed in claim 15 wherein, the said salt used for drying the extract is sodium sulphate.

21. A process as claimed in claim 15 wherein, the chromatography employed for purification is column chromatography.

22. A process as claimed in claim 15 wherein, the gel used for chromatography is silica gel.

23. A process as claimed in claim 15 wherein, the eluant used for chromatography is hexane-chloroform mixture.

* * * * *